United States Patent [19]
Lavon et al.

[11] Patent Number: 6,013,657
[45] Date of Patent: Jan. 11, 2000

[54] PHARMACEUTICAL COMPOSITIONS CONTAINING MUPIROCIN

[75] Inventors: Ilana Lavon; Chalil Abu-Gnim, both of Beer-Sheva; Amira Zeevi, Omer; Yoav Raechav; Shifra Katz, both of Beer-Sheva; Joseph Kaspi, Givatayim, all of Israel

[73] Assignee: AGIS Industries Ltd., Israel

[21] Appl. No.: 09/111,554

[22] Filed: Jul. 8, 1998

[30] Foreign Application Priority Data

Feb. 2, 1998 [IL] Israel ........................................ 123143

[51] Int. Cl.⁷ .................................................... A61K 31/35
[52] U.S. Cl. ............................................................. 514/330
[58] Field of Search ............................................... 514/460

[56] References Cited

U.S. PATENT DOCUMENTS

| | | | |
|---|---|---|---|
| 4,524,075 | 6/1985 | Oduro-Yeboah | 514/451 |
| 4,790,989 | 12/1988 | Hunter et al. | 424/404 |
| 5,378,451 | 1/1995 | Gorman et al. | 424/47 |

FOREIGN PATENT DOCUMENTS

WO 95/10999  4/1995  WIPO.

OTHER PUBLICATIONS

J. Peter Clayton et al.; The Chemistry of Pseudomonic Acid. Part 3. The Rearrangement Of Pseudomonic Acid A In Acid And Basic Solution; "J.C.S. Perkin I"; pp. 838–846; 1979.

H. Rode et al., Bacterial Efficacy Of Mupiroci In Multi–Antibiotic Resistant *Staphylococcus aureus* Burn Wound Infection; "Journal of Antimicrorbial Chemotherapy"; pp. 589–595; 1988.

E.B. Kaczmarski et al.; Correspondence; "Journal of Antimicrobial Chemotherapy"; pp. 771–776; 1988.

Bernard D. Davis et al.; Correspondence; "Journal of Antimicrobial Chemotherapy"; pp. 78–79; 1988.

Horst Hermsdorf; Saturated Triglycerides And Their Derivatives In Cosmetic Creams And Lotions; "Creams and Lotions, Documentary/Formulary" vol. 95; pp. 61–63; Apr. 1980.

James E. F. Reynolds; Martindale The Extra Pharmacopeia; 31st edition; p. 251; 1996.

The Merck Index, 12th edition, p. 6968, 1996.

*Primary Examiner*—Phyllis G. Spivack
*Attorney, Agent, or Firm*—Pendorf & Cutliff

[57] ABSTRACT

The invention provides a chemically stable composition comprising a therapeutically effective amount of mupirocin, in a carrier selected from the group consisting of oleyl alcohol, castor oil and a mixture thereof, the composition further optionally comprising a pharmaceutically acceptable base.

12 Claims, No Drawings

PHARMACEUTICAL COMPOSITIONS CONTAINING MUPIROCIN

The present invention relates to improved pharmaceutical formulations which contain Mupirocin as the therapeutic agent.

Mupirocin is an antibiotic produced by fermentation of *Pseudomonas fluorescens*, and it is mainly active against gram-positive aerobes (Martindale, p. 251, 1986). This antibiotic agent is useful in treating skin, ear and eye disorders, including impetigo. A commercial preparation of mupirocin as an ointment is available under the brand name of Bactroban®.

Mupirocin is not a stable molecule. It tends to undergo hydrolysis and rearrangement reactions in the presence of water, acid and base (Clayton J P. et al., The chemistry of pseudomonic acid. part 3. Rearrangement of pseudomonic acid A in acid and basic solution, J. C. S. Perkin, 838–846, 1979). Hence, the conditions in which Mupirocin is stable, are limited. Due to this fact, stable formulations which contain Mupirocin are rare to find.

U.S. Pat. No. 4,524,075 claims several stable formulations of mupirocin containing PEG as an inactive ingredient. The PEG is claimed to stabilize the mupirocin in the formulations. However, a limited stability data is given only for an ointment which comprises of mupirocin dissolved in a PEG ointment USP base with the commercial name of Bactroban® (a mixture of PEG 400 and PEG 4000), and for liquid formulation of mupirocin dissolved in PEG 400.

Formulations based on polyethylene glycols suffer from several drawbacks, which in this case, limit the use of the ointment. Such formulations are not suitable for application to mucous membranes. In spite of excellent results seen in a study in rats when Mupirocin 2% in a PEG Ointment was applied to burn wounds, this ointment is not recommended for use in patients with burns nor for patients with open wounds and damaged skin, due to the possible toxicity of the polyethylene glycol base (Rode H. et al. Bactericidal efficacy of Mupirocin in multi-antibiotic resistant *staphylococcus aureus* burn wound infection, J. Antimicrob Chemother 1988, 21, 589–95; Kaczmarski E B, Mupirocin in polyethylene glycol base is not suitable for application to burns, J. Antimicrob. Chemoter, 1988, 22, 771–6; and Rode H., et al. Mupirocin in a polyethylene glycol carrier base, J. Antimicrob. Chemoter, 1989, 24, 78–9). In addition PEGs are known to be potential skin irritants (Martindale, p. 251, 1986).

World patent WO95/10999 claims a cream formulation containing mupirocin or a salt thereof. Experiments have proven however that mupirocin formulated as a cream is not sufficiently stable. A cream formulation based on this patent is given in example 1. The purity of mupirocin in this product was reduced to 78% after 7 days in 40° C.

| Comparative Example # 1 | Cream Formulation |
| --- | --- |
| Mineral oil | 52.8% |
| Tween-80 | 6% |
| Stearyl alcohol | 3.5% |
| Cetyl alcohol | 3.5% |
| Xanthan gum | 0.2% |
| Water | 32% |
| Mupirocin | 2% |

U.S. Pat. No. 4,790,989 describes formulations of mupirocin for the treatment of fungal infections in which the mupirocin is not dissolved in the formulation (less than 1% of the mupirocin was dissolved). There are no commercially available preparation of mupirocin indicated for fungal infections.

The present invention relates to stable pharmaceutical formulations of mupirocin. These formulations are also non-toxic, non-irritant and are suitable for application on mucosal membranes.

Thus, according to the present invention, there is now provided a chemically stable composition comprising a therapeutically effect amount of mupirocin, in a carrier selected from the group consisting of oleyl alcohol, castor oil and a mixture thereof, said composition further optionally comprising a pharmaceutically acceptable base.

These new compositions do not suffer from the drawbacks mentioned above and hence have an advantage over the commercial preparation available in the market. Due to their non-toxicity, their range of application can be wider in that they can be applied on mucosal membranes (e.g. for nasal application), and can be applied on open wounds, burn wounds etc. Moreover, due to its oleaginous characteristic, the carrier has an excellent skin compatibility, spreads well on the skin and penetrates easily (Hermsdorf H., Saturated triglycerides and their derivatives in cosmetic creams and lotions, Cosmetic and toiletries, 1980, 95, 61–63). The formulations of the present invention may be presented in the form of an ointment, cream, lotion, eye ointment, eye and ear drop, nasal ointment, as well as in other conventional topical application formulations.

In general, the formulation consists of Mupirocin dissolved in a suitable solvent or a mixture of solvents, which is opptionally mixed with a hard fat base, such as triglyceride optionally with the aid of other excipients such as surfactants.

As stated hereinbefore, Mupirocin does not dissolve in classic pharmaceutical solvents such as glycerol and mineral oil. Examples of other pharmaceutical acceptable solvents which do not dissolve Mupirocin are caprylic-capric triglyceride, isopropyl myristate, isopropyl palmitate, octyl dodecanol (Eutanol G) and isopropyl stearate.

In pharmaceutical acceptable solvents, in which Mupirocin did dissolve, its stability was insufficient. Examples are butylene glycol, ethylene glycol, propylene glycol, isopropanol and glycerol mixture, propylene glycol and mineral oil mixture, propylene glycol and glycerol mixture.

Therefore, it was surprising to find that solvents like, oleyl alcohol and castor oil stabilize Mupirocin. Castor oil is especially interesting due to its unique behavior. Other fixed oils that were tested, do not dissolve Mupirocin. These oils include sesame oil, sunflower oil, sweet almond oil and olive oil.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

The stability of Mupirocin in various acceptable pharmaceutical solvents and mixtures thereof was tested by heating a 2% solution to 80° C. for 24 hr. As a stability reference a solution of 2% Mupirocin in PEG-400 (a component of Bactroban®) as well as Bactroban®, were used.

The results are presented in table 1.

TABLE 1

| Type of Solvent | % purity after heating for 24h at 80° C. |
|---|---|
| Bactroban ® | 92.5 |
| PEG-400 | 93.8 |
| castor oil | 94.3 |
| oleyl alcohol | 91.0 |
| isostearyl alcohol | 84.9 |
| 1,3 butylene glycol | 80.3 |
| isopropanol + glycerol | 72.6 |
| propylene glycol + mineral oil | 55.6 |
| propylene glycol | 50.4 |
| ethylene glycol | 2.7 |

It was further found that a classic base such as petrolatum is unsuitable in this case due to physical incompatibility between the base and the solvents.

Thus, in preferred embodiments of the present invention there is provided an ointment comprising a therapeutically effect amount of mupirocin, dissolved in a carrier selected from the group consisting of oleyl alcohol, castor oil and a mixture thereof, in combination with a hard fat, e.g., triglyceride and optionally other additives such hydrophobic and/or hydrophilic surfactants which improve physical stability. The inactive ingredients of this base does not affect the stability of mupirocin and hence, provide a stable vehicle. Formulating this base together with a different solvent such as isostearyl alcohol, which exhibits a moderate stability in the 80° C./24 hr. test, does not provide sufficient stability behavior, as presented in example 2.

| Comparative Example # 2 | Ointment formulation |
|---|---|
| Hard Fat (capric-caprylic-stearic triglyceride) | 80% |
| Isostearyl Alcohol | 10% |
| Propylene Glycol Stearate | 8% |
| Mupirocin | 2% |

The purity of this formulation was reduced to 93.4% after 4 months in 25° C., and to 92.1% after the same period of time in 30° C. These results emphasize the significance and unique role that the castor oil and oleyl alcohol play as stabilizers for Mupirocin.

The invention is illustrated by the following examples:

| Example # 3 | Ointment Formulation |
|---|---|
| Hard Fat (capric-caprylic-stearic triglyceride) | 78% |
| Oleyl Alcohol | 20% |
| Mupirocin | 2% |

| Example # 4 | Ointment Formulation |
|---|---|
| Hard Fat (capric-caprylic-stearic triglyceride) | 70% |
| Oleyl Alcohol | 20% |
| Propylene Glycol Stearate | 8% |
| Mupirocin | 2% |

| Example # 5 | Ointment Formulation |
|---|---|
| Hard Fat (capric-caprylic-stearic triglyceride) | 77.5% |
| Castor Oil | 12.5% |
| Propylene Glycol Stearate | 8% |
| Mupirocin | 2% |

| Example # 6 | Ointment Formulation |
|---|---|
| Hard Fat (capric-caprylic-stearic triglyceride) | 65% |
| Hard Fat (hydrogenated coco glycerides) | 5% |
| propylene glycol stearate | 8% |
| Oleyl Alcohol | 10% |
| Caster oil | 10% |
| Mupirocin | 2% |

| Example # 7 | Ointment Formulation |
|---|---|
| Hard Fat (capric-caprylic-stearic triglyceride) | 70% |
| p.g.stearate | 8% |
| oleyl alcohol | 5% |
| castor oil | 15% |
| Mupirocin | 2% |

| Example # 8 | Ointment Formulation |
|---|---|
| Hard Fat (capric-caprylic-stearic triglyceride) | 70% |
| Castor oil | 20% |
| Propylene Glycol Stearate | 8% |
| Mupirocin | 2% |

| Example # 9 | Ointment Formulation |
|---|---|
| Hard Fat (capric-caprylic-stearic triglyceride) | 68% |
| Castor oil | 22% |
| Propylene Glycol Stearate | 8% |
| Mupirocin | 2% |

The formulations are produced by melting the mixture of Hard Fats and propylene glycol stearate and stirring in the solution of Mupirocin in its solvents.

| Example # 10 | Ointment Formulation |
|---|---|
| Hard Fat (capric-caprylic-stearic triglyceride) | 69.5% |
| Oleyl Alcohol | 20% |
| Sucrose Stearate | 0.5% |
| Propylene Glycol Stearate | 8% |
| Mupirocin | 2% |

| Example # 11 | Drop Formulation |
|---|---|
| Castor Oil | 98% |
| Mupirocin | 2% |

The formulation of Example 11 was produced by heating castor oil to 50° C. and stirring in Mupirocin until it completely dissolved. The solution can undergo a sterilization process, if needed.

Stability test of these formulations in various conditions was compared with the commercial product, Bactroban® (Mupirocin 2% in a PEG Base).

Table 2 presents typical results:

TABLE No. 2

| | Purity of Mupirocin | | | | | | | | | | | |
|---|---|---|---|---|---|---|---|---|---|---|---|---|
| | 1 month | | | 2 months | | | 3 months | | | 4 months | | |
| Formulation | 25° C. | 30° C. | 40° C. | 25° C. | 30° C. | 40° C. | 25° C. | 30° C. | 40° C. | 25° C. | 30° C. | 40° C. |
| Bactroban ® | | 94.4 | 93.7 | | | | | | | | | |
| example 3* | 95.9 | 95.6 | | 95.9 | 95.6 | | 95.8 | 95.8 | | 95.7 | 96.0 | |
| example 4* | 95.7 | 95.6 | | 95.9 | 95.5 | | 95.5 | 95.1 | | 95.1 | | |
| example 5* | 96.0 | 96.5 | 94.6 | 96.6 | 96.2 | 94.7 | | | | | 94.4 | 96.5 |
| example 6* | | 96.5 | | 65.2 | 95.5 | | 96.2 | 95.5 | | | | |
| example 7* | 96.6 | 96.1 | 95.0 | | | | | | | | | |
| example 5* | 96.0 | | 94.6 | 95.0 | | | | | | | | |

*note:
the purity of mupirocin batches used in the formulation of examples 3–8 is in the 96%–97% range It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A chemically stable composition comprising a therapeutically effective amount of mupirocin, in a carrier selected from the group consisting of oleyl alcohol, castor oil and a mixture thereof, said composition further optionally comprising a pharmaceutically acceptable base.

2. A composition according to claim 1, further optionally comprising other pharmaceutically acceptable additives.

3. A composition according to claim 2, wherein the pharmaceutical additives are hydrophobic and/or hydrophilic surfactants.

4. A composition according to claim 3, wherein the hydrophobic surfactant is propylene glycol stearate.

5. A composition according to claim 3, wherein the hydrophilic surfactant is a sucrose ester.

6. A composition according to claim 5, wherein the sucrose ester is chosen from sucrose stearate, sucrose palmitate, sucrose oleate and sucrose myristate.

7. A composition according to claim 1, comprising from 1 to 99% of castor oil.

8. A composition according to claim 1, comprising from 1 to 99% of oleyl alcohol.

9. A composition according to claim 1, comprising a mixture of castor oil and oleyl alcohol.

10. A composition according to claim 1, wherein said base is a hard fat ointment base.

11. A composition according to claim 10, wherein the concentration of the hard fat is between 10% and 90%.

12. A drop formulation according to claim 1 which comprises 1–5% mupirocin dissolved in castor oil.

* * * * *